(12) United States Patent
López Vidal et al.

(10) Patent No.: US 7,666,437 B2
(45) Date of Patent: Feb. 23, 2010

(54) **INTRANASAL VACCINE FOR USE AGAINST DISEASE CAUSED BY ENTEROTOXIGENIC *ESCHERICHIA COLI***

(75) Inventors: Yolanda López Vidal, Delegación Coyoacan (MX); Olga Roxana Suaste Villanueva, Delegación Coyoacan (MX); Ricardo Godinez Moreno, Delegación Coyoacan (MX); Luis José Arredondo Hernández, Delegación Coyoacan (MX)

(73) Assignee: Universidad Nacional Autonoma de Mexico, Mexico (MX)

( * ) Notice: Subject to any disclaimer, the term of this patent is extended or adjusted under 35 U.S.C. 154(b) by 42 days.

(21) Appl. No.: 12/092,946

(22) PCT Filed: Oct. 26, 2006

(86) PCT No.: PCT/MX2006/000116

§ 371 (c)(1),
(2), (4) Date: Aug. 13, 2008

(87) PCT Pub. No.: WO2007/073137

PCT Pub. Date: Jun. 28, 2007

(65) Prior Publication Data

US 2009/0028909 A1  Jan. 29, 2009

(30) Foreign Application Priority Data

Nov. 8, 2005  (MX) .................. PA/A/2005/011997

(51) Int. Cl.
*A61K 39/108* (2006.01)
*A61K 39/38* (2006.01)
*A61K 39/00* (2006.01)
*A61K 39/02* (2006.01)
*A61K 38/04* (2006.01)

(52) U.S. Cl. .............. 424/241.1; 424/184.1; 424/185.1; 424/234.1; 530/300; 530/326

(58) Field of Classification Search ....................... None
See application file for complete search history.

(56) References Cited

U.S. PATENT DOCUMENTS

2003/0161889 A1 * 8/2003 Reid et al. .................. 424/491

OTHER PUBLICATIONS

Lopez-Vidal et al. Continous and Common Epitopes Present in Fimbria. Gaceta Medica De Mexico. Nov.-Dec. 1997; 133 (6):511-525.*

* cited by examiner

*Primary Examiner*—Robert Mondesi
*Assistant Examiner*—Oluwatosin Ogunbiyi
(74) *Attorney, Agent, or Firm*—Miller Matthias & Hull

(57) ABSTRACT

The disclosure relates to an intranasal peptide vaccine for use against infection caused by enterotoxigenic *Escherichia coli* (ETEC), containing a common linear protein epitope known as CLE which is recognized by sera of patients infected with the bacteria and which is associated with a mucosal adjuvant comprising cholera toxin subunit B, known as CTB. The disclosure relates to a peptide containing twenty amino acids, which is located in the linear sequence of the CFA/I fimbria of enterotoxigenic *Escherichia coli*.

13 Claims, 4 Drawing Sheets

Figure 1

| Day | Group | Presence of ETEC in feces | Diarrhea |
|---|---|---|---|
| 0 | Control | - | 0 |
|   | CLE | - | 0 |
|   | CTB | - | 0 |
|   | CLE+CTB | - | 0 |
| 1 | Control | ++++ | 0 |
|   | CLE | ++++ | 0 |
|   | CTB | ++++ | 0 |
|   | CLE+CTB | ++++ | 0 |
| 3 | Control | +++ | 1 |
|   | CLE | ++ | 1 |
|   | CTB | ++ | 1 |
|   | CLE + CTB | + | 0 |
| 4 | Control | - | 0 |
|   | CLE | - | 1 |
|   | CTB | - | 0 |
|   | CLE + CTB | - | 0 |
| 7 | Control | - | 0 |
|   | CLE | - | 0 |
|   | CTB | - | 0 |
|   | CLE + CTB | - | 0 |

Figure 4

| Group | n | Diarrhea | | Excretion of ETEC (days) |
|---|---|---|---|---|
| | | Sick (%) | Duration (days) | |
| Control | 11 | 82 | 2.45 | 5.75 |
| Immunized | 11 | 18 | 0.36 | 2.4 | n = number of used animals

Figure 5

| Group | n | Anti-CLE (Absorbance ± SD) | Anti-CFA/I (Absorbance ± SD) |
|---|---|---|---|
| Control | 7 | 0.631 ± 0.44 | 3.384 ± 0.242 |
| Immunized | 6 | 1.644 ± 0.23 | 3.457 ± 0.310 |
| p Value | | 0.000095 | 0.74258 | n = number of used animals

Figure 6

| Group | n | Sample (serum) | Anti-CLE | Anti-CFA/I | Anti-CTB | Anti-LT |
|---|---|---|---|---|---|---|
| Control | 11 | Final time | < 1.4 | < 1.4 | < 1.4 | < 1.4 |
| Immunized | 11 | Final time | 2.8 | 2.9 | 3.7 | 3.7 | n = number of used animals, final time = 8 days after the challenge

INTRANASAL VACCINE FOR USE AGAINST DISEASE CAUSED BY ENTEROTOXIGENIC ESCHERICHIA COLI

FIELD OF THE DISCLOSURE

The present disclosure is related to the use of peptides for the purposes of vaccination, specifically it relates to peptides that induce a immune response in mucosa and more specifically it is related to a peptide included in a intranasal vaccine composition to elicit a protective immune response in mammals against illness caused by enterotoxigenic *Escherichia coli*.

BACKGROUND OF THE DISCLOSURE

At present it is estimated that over 1,500 million cases of diarrhea occurred every year worldwide, of which, 3 million ended in death. Of the total number of cases of diarrhea, 210 million are caused by the bacterium enterotoxigenic bacterium *Escherichia coli*, hereinafter designated as ETEC, of these episodes 380,000 cases ended in death (World Health Organization (WHO) State of the art of new vaccines Research & Development Initiative for Vaccine Research; Geneva, April 2003). Although the diarrhea caused by this microorganism occurs in groups of all ages, the mortality is more common in children under 5 years old, particularly when this illness occurs concomitantly with malnutrition, thereby the developing countries are specially affected. This bacterium also is the principal causal agent of the so-called traveler's diarrhea.

ETEC infection is acquired orally, principally through contaminated drinks or food; the bacterium overcomes the acidic conditions of the stomach until it reaches the small intestine, where, due to its Colonization Factor Antigens known as CFA's, it adheres to the intestinal mucosa and liberates its enterotoxins which are principally two, heat-labile enterotoxin known as LT and heat-stable enterotoxin or ST which are the factors responsible for the diarrhea (Gaastra W, Svennerholm A M. Colonization factors of human enterotoxigenic *Escherichia coli* (ETEC). Trends in Microbiology. 1996; 4(11): 444-452).

More than 20 different CFA's have been described in the literature, and of these three have been identified as the more prevalent, and they are known as CFA/I, CFA/II and CFA/IV that were reported by several authors, since there was detected between 50 to 75% of ETEC strains isolated from patients suffering from diarrhea all over the world, including Mexico, the majority are grouped in the family CFA/I. (Gaastra W, Svennerholm A M. Colonization factors of human enterotoxigenic *Escherichia coli* (ETEC). Trends in Microbiology. 1996; 4(11): 444-452. López-Vidal Y, Calva J J, Trujillo A, Ponce de León A, Ramos A, Svennerholm A-M, Ruiz-Palacios G M. Enterotoxins and adhesins of enterotoxigenic *Escherichia coli* are they a risk factor for acute diarrhea in the community? J Infect Dis 1990; 162:442-447, and Steinsland H, Valentiner-Branth P, Gjessing H K, Aaby P, Molbak K, Sommerfelt H. Protection from natural infections with enterotoxigenic *Escherichia coli*: Longitudinal study. The Lancet. 2003; 362). These types of CFA's induce protective immunity against the bacterium and they are pointed out as the most important among the strategies for the development of effective vaccines. (Middlebrook J L, Dorland R B. Bacterial Toxins: Cellular mechanisms of Action. Microbiological Reviews. 1984; 48(3): 199-221. McConell M M, Hibberd M L, Penny M E, Scotland S M, Cheasty T, Rowe B. Surveys of human enterotoxigenic *Escherichia coli* from three different geographical areas for possible colonization factors. Epidemiol. Infect. 1991; 106: 477-484).

Due to the epidemiological importance of ETEC, many of the efforts have been directed to the prevention of the illness by obtaining an effective and safe vaccine, (Levine M M, Kaper J B, Black R E, Clements A M. New Knowledge on Pathogenesis of Bacterial Enteric Infections as Applied to Vaccine Development. Microbiological Reviews. 1983; 47(4):510-550) however, to the date these efforts have been unsuccessful and a product that satisfies these needs has not been placed in the market yet. (World Health Organization [WHO] State of the art of new vaccines Research & Development Initiative for Vaccine Research; Geneva, April 2003).

One of the vaccines that is under development and that has passed to the phase of trials in human healthy volunteers from different geographical regions, was prepared in the University of Götemburg in Sweden, and it is based on subunit B of cholera toxin combined with 5 formalin inactivated strains of ETEC, which all together express the CFA's of most epidemiological importance on a global scale. (Quadri F, Ahmed T, Ahmed F, Sack B, Sack A, Svennerholm A M. Safety and Immunogenicity of an oral, inactivated enterotoxigenic *Escherichia coli* plus cholera Toxin B subunit vaccine in Bangladeshi children 18-36 months of age. Vaccine 2003; 21:2394-2403).

Other strategies for the development of vaccines have focused on the use of live bacteria, as it is seen in the work realized in the Center for Development of Vaccines CVD of the University of Maryland, using *Shigella* as vector for the expression of colonization factors and enterotoxins from ETEC. (Barry E M, Altboum Z, Losonsky G, Levine M M. Immune responses elicited against multiple enterotoxigenic *Escherichia coli* fimbriae and mutant LT expressed in attenuated *Shigella* vaccine strains. Vaccine 2003; 21:333-340).

Recently a vaccine has been prepared with a new technology of administration; by means of a patch for transdermal immunization containing the surface component of *E. coli* known a CS6 and the heat-labile toxin known as LT; which has been already tested in human volunteers, where an immune response of Th1 and Th2 type characterized by IgG2a and IgG1 respectively, was determined (Wenneras C, Firdausi Q, Prodeep K B, Bladley S and Svennerholm A-M. Intestinal Immune Responses in patients Infected with Enterotoxigenic *Escherichia coli* and in vaccinees. Infect. Immun. 1999; 66:3311-3316. Quadri F, Ahmed T, Ahmed F, Sack B, Sack A, Svennerholm A M. Safety and Immunogenicity of an oral, inactivated enterotoxigenic *Escherichia coli* plus cholera Toxin B subunit vaccine in Bangladeshi children 18-36 months of age. Vaccine. 2003; 21: 2394-2403. Byrd, W., and F. J. Cassels. 2003. Mucosal immunization of BALB/c mice using enterotoxigenic *Escherichia coli* colonization factors CFA/I and CS6 administered with and without a mutant heat-labile enterotoxin. Vaccine 21: 1884-1893. Helander A, Wenneras C, Quadri F, Svennerholm A M. Antibody Responses in Humans against *Coli* Surface Antigen 6 of Enterotoxigenic *Escherichia coli*. Infection and Immunity. 1998; 66(9):4507-4510). However, the immune response against the colonization factors was not consistent as shown by the prevalence of the illness in different geographical regions.

There is other type of developed strategies that including vaccines formed by colonization factors encapsulated in microspheres, or by means of the expression of the subunit B of LT in plants of tobacco, potatoes, tomatoes and bananas, but these strategies are highly expensive and nevertheless the conferred protection is low.

Another option can be a vaccine prepared with the common linear epitope of immuno-dominant sequences from CFA's which offered a broader spectrum and increases the level of protection from the ETEC infection (López-Vidal Y, Epitopos continuos y comunes presentes en las fimbrias de *Escherichia coli* enterotoxigénica (ETEC). Gac. Med. Mex. 1997; 133 (6): 511-525. Domínguez M, et al. Colonization Factor Antigenic I Peptide as Intranasal Vaccine Approach against enterotoxigenic *Escherichia coli* infection in hamsters. 5th National Symposium, Basic Aspects of vaccines, 1999).

Generally we can recount that different types of vaccines have been evaluated against diarrhea caused by ETEC and although many of these vaccines have demonstrated protective effectiveness against ETEC infection, some of them show certain side effects; another important problem to be considered in the design of vaccines against ETEC, is the variability in the prevalence of the different colonization factors, which prompted us to design a vaccine that is effective and safe against the different ETEC serotypes.

Intranasal administration can be an additional alternative for a vaccine against ETEC, which would add additional advantages, providing superiority over other vaccines. In this respect a great number of studies has been performed that demonstrated that the mucosa-associated lymphoid tissue known as MALT, is a common system, that is, that the stimulation in a certain site of the mucosa also known as inductor site elicits a response at local level, remotely or in the effector site, this represented a great advantage in vaccine design, with the form of transmucosal administration being greatly facilitated (Cripps A W, Kyd J M, Foxwell A R, Vaccines and Mucosal immunization. Vaccine 2001; 19:2513-2515). The use of the intranasal route as route of administration has as principal advantages the presence of a highly vascularized greater surface, the elimination of the use of syringes with the risk that this poses, the decrease of administered doses compared to the oral route which involves a decrease of adverse effects, easy administration, application to a great number of persons in relatively short times and the induction of antibodies and cells of the immune response (Zuercher A W. Upper Respiratory Tract Immunity. Viral Immunology 2003; 3; 279-289). There are studies that demonstrate that the intranasal administration can stimulate the production of secretory IgA at intestinal level, which provides a great advantage in the development of vaccines directed to the protection against intestinal pathogens (Hong-Yin Wu, Russell M W. Induction of mucosal and systemic immune responses by intranasal immunization using recombinant cholera toxin B subunit as an adjuvant. Vaccine 1998; 16(2/3):286-292).

Vaccine strategies to improve immunity at the level of the mucosa include the use of these alternate routes together with adjuvants. (Colonization Factor Antigenic I Peptide as Intranasal Vaccine Approach against enterotoxigenic *Escherichia coli* infection in hamsters. Domínguez M, et al. 5th National Symposium, Basic Aspects of vaccines, 1999). Recently, nasal mucosa has been used as inductive site that has showed to increase the immune response at level of the mucosa both locally and distally such as in intestinal mucosa, respiratory mucosa and genital mucosa. Administering certain antigen to the mucosa associated to lymphoid tissue is a way of eliciting immune response in sites distal from mucosa. (Byrd, W, and F. J. Cassels. 2003. Mucosal immunization of BALB/c mice using enterotoxigenic *Escherichia coli* colonization factors CFA/I and CS6 administered with and without a mutant heat-labile enterotoxin. Vaccine 21:1884-1893. Van Ginkel F W, Nguyen H H, McGhee J R, Vaccines for Mucosal Immunity to Combat Emerging Infectious Diseases. Emerging Infectious Diseases. 2000; 6(2):123131.)

For the above, is still of great relevance to count with an effective vaccine against ETEC infection that can be applied globally and through a route of administration that allows a rapid, easy application and that could minimize the adverse effects that could be generated.

The present disclosure relates to a peptide vaccine that can be administered intranasally, containing a common linear protein epitope from different ETEC colonization factors that can be recognized by sera of patients infected with said bacteria.

BRIEF DESCRIPTION OF DRAWINGS

FIG. 1 shows a summary of post-immunization results obtained from mice with CLE, CTB or the vaccine and from a control group that later was infected by ETEC H 10407; the percent of ETEC excretion is shown where: – corresponds to negative; + corresponds to 25%; ++ corresponds to 50%; +++ corresponds to 75%, and ++++ corresponds to 100%, and in respect to the occurrence of diarrhea: 0=no diarrhea; 1=loss of consistency of feces but without wet tail; 2=wet perianal region and tail, and 3=tail, paws and low abdomen wetted and with an inactive appearance. In this figure it can be appreciated that the developed vaccine has the ability to decrease bacterial excretion in addition to the signs of diarrhea, which is evident on day 3 after the infection.

FIG. 4 shows the evaluation of ETEC infection that expresses CFA/I in a golden Syrian hamster model after vaccine administration where it can be observed that in the vaccinated animals there a decrease both the percentage of sick hamsters and the duration of diarrhea when compared to the control group, it can also observed that there is a decrease of the time of ETEC excretion.

FIG. 5 shows the levels of IgG antibodies against CLE and CFA/I of ETEC from vaccinated hamsters and control, 11 days after the infection with ETEC CFA/I where it can be appreciated that a significant increase occurs in IgG antibodies titre against CLE in the animals after the vaccination.

FIG. 6 shows antibody titres against CLE, CFA/I, CFA/II, CTB and LT in vaccinated hamsters and control 8 days after infection with ETEC and it can be appreciated clearly that after the vaccination higher titres of antibodies against CLE, CFA/I, CFA/II, CTB and LT were generated.

DETAILED DESCRIPTION

Figure 2:
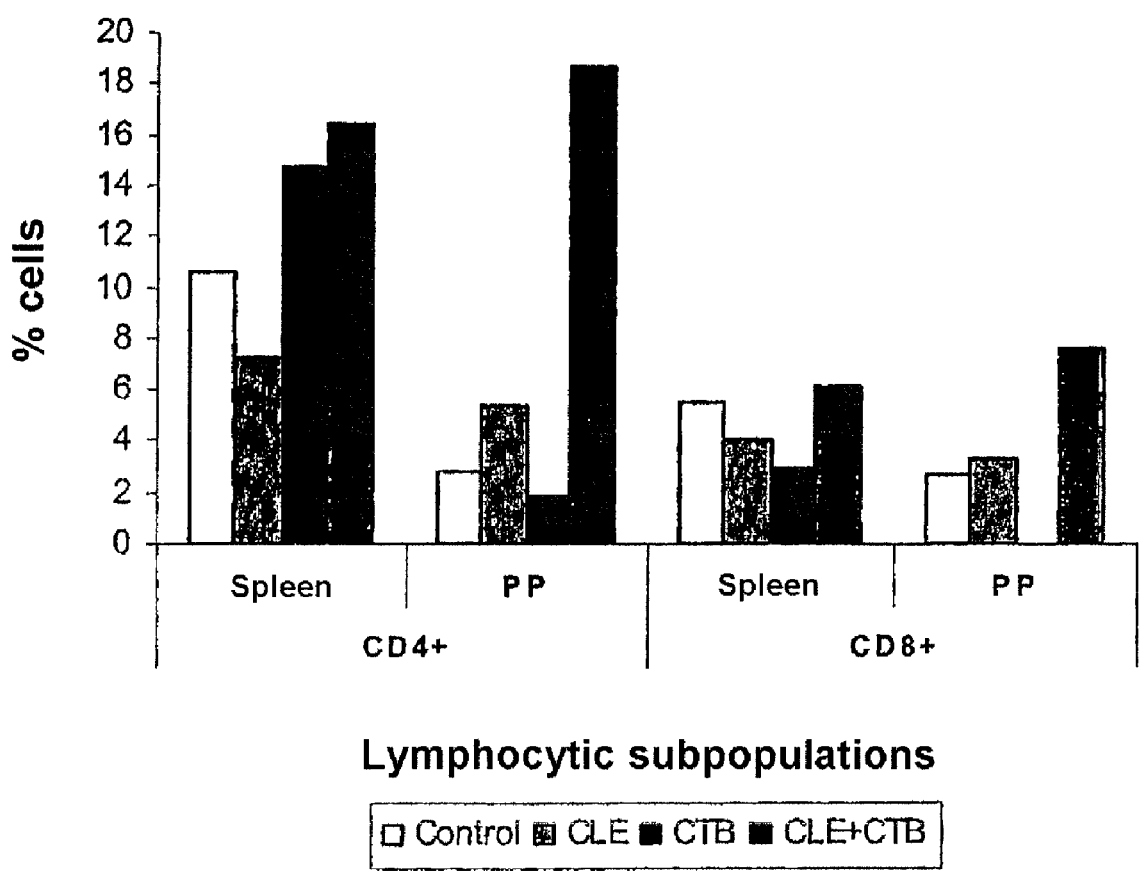
FIG. 2 shows the results corresponding to subpopulations of CD4+ and CD8+ T lymphocytes of cells obtained from the spleen and Peyer patches after immunization of mice with CLE, CTB or the vaccine and a control group that later was infected by ETEC H10407 where it can be seen generally that the highest percentage of CD4+ and CD8+ T lymphocytes was obtained by the group vaccinated both in spleen and in Peyer patches.

For the development of this vaccine, first the immune response that elicited the linear common epitope known as CLE associated to mucosal adjuvant, cholera toxin B subunit known as CTB, in a murine model and in a Syrian golden hamster model was characterized. Starting from the entire fimbria CFA/I, a 20 amino acids peptide amino acids named as CLE was identified and studied, said peptide is located in the linear sequence of enterotoxigenic *Escherichia coli* CFA/I fimbria from amino acid 33 to amino acid 52 herein identified as SEQ ID NO: 1, which contains a terminal cysteine in position 53, included to form protein complexes such as dimers, trimers and pentamers, with the trimers being predominant at 37° C., such that it will have stability in its configuration and its ability to facilitate recognition by class II receptor from major histocompatibility complex and T lymphocyte receptor could be increased. This peptide is capable of eliciting immune protective response against the principal serotypes of ETEC.

Synthesis of CLE was performed by conventional methods. CTB was purchased from Merieux Laboratory, France.

In order to elucidate the sequence of peptide CLE, the characterization of common linear epitopes for different fimbrias of ETEC was carried out, by means of synthesis of continuous octapeptides spanning the entire sequence of the colonization factor antigen I designated as CFA/I; using the method of Geysen in which the synthesis of peptides was carried out in polyethylene sticks such that each of them corresponded to each of the wells of an ELISA plate. This arrangement enabled the study of recognition by antibodies against sera from children under five years old who were afflicted with ETEC infection, sera of adults from endemic and not endemic zones, hyperimmune sera that were prepared by immunization of rabbits with ETEC strains carrying different colonization factors and anti-CFA/1 monoclonal sera. The essay was performed similar to an ELISA. Most of the sera from children belonging to the convalescent stage recognized all the octapeptides, with the recognition being higher for three of said octapeptides, same that were recognized by serum from an adult belonging to an endemic area. Whereas the anti-CFA/1 monoclonal antibody did not recognized any peptide. The recognition of octapeptides was designated epitopes.

The identification of common and continuous epitopes in CFA/I by hyperimmune heterologous sera was very variable and it depended on each of the sera, and it was found that the colonization factors with higher similarity and that exhibited crossed antigenic response were CFA/I, the surface components of coli 1, 3 and 4 designated as CS1, CS3, CS4 and the putative colonization factor 0166 or PCF0166 and part of the sequence from common linear epitope CLE was recognized on these elements. CLE was selected because it was recognized by 100% of the children's sera after natural infection and by sera of adults from endemic areas for ETEC. From this finding, the peptide vaccine CLE of the colonization factors with B subunit B of cholera toxin CTB was developed in our laboratory, whose administration was the intranasal route due to the already mentioned advantages.

Analysis of CLE Structure

SEQ ID NO: 1

Circular Dichroism: A solution of 100 µg/mL of CLE in trifluoroethane was used for the readings using a quartz cell of with 1 cm of optical pathway. Measurements were carried out in a JASCO J-715 spectrophotometer. The obtained spectrum is the average of five readings.

The spectrum of circular dichroism for CLE in PBS at pH 7.4 and room temperature 20° C., suggests the formation of a secondary structure. The spectrum indicates that CLE from CFA possesses a predominant structure of beta sheet that agrees with the prediction of a secondary structure performed in the Antheprot 5.0 software.

Dynamic light scattering: One milliliter of 1 mg/ml CLE diluted in 10 mm PBS, pH 7.4 was used to evaluate the dynamic light scattering at different temperatures of 5, 15, 25, 35 and 37° C. Hydrodynamic diameter of CLE was determined using the Zed ziser nano series (Mc Malvern, USA). It was found that CLE has the ability to form trimeric structures at physiological conditions of pH and temperature.

Having properly characterized CLE and evaluated its ability to elicit an protective immunological response, we proceed to develop a vaccine composition integrated with such a relation in its components, which enables to potentiate the protective effect of CLE, in this disclosure it is used preferably in a proportion of 8 parts of CLE to one part of a suitable adjuvant for use in mucosa, in this case the adjuvant CTB was used in a pharmaceutically acceptable aqueous vehicle for intranasal application in a pharmacologically effective dose, without the use of this adjuvant is limitative, simply it appears like selected in this form of the disclosure. The proportion used in this vaccine composition will vary according to the used adjuvant.

EXAMPLES

The following examples are presented to provide a better understanding of the subject matter disclosed herein and they are not intended to limit the disclosure to the same.

Example 1

Demonstration of the Ability of Peptide CLE to Elicit Protective Immune Response Against ETEC Peptide CLE was applied to pathogen-free, 6 to 8 weeks old, female BALB/c mice, which were randomly distributed into groups of five animals in each group. Peptide CLE, corresponding to SEQ ID NO: 1, was administered in a pharmacologically effective dose, that for this case was 50 µg/mL in a volume of 7.5 µL per mouse, intranasally, three times at 0, 7 and 28 days. The control group was provided with phosphate buffered solution PBS orally. The challenge was carried out one week after the last immunization, by administering by gastric route an inoculum of $6 \times 10^8$ CFU of strain H10407 of ETEC.

To evaluate the conferred protection, parameters such as the excretion of ETEC in feces by means of coproculture and identification by means of hemagglutination test in the presence of D-mannose were determined, (López-Vidal Y. Colonization Factor antigens of Enterotoxigenic *Escherichia coli* (Monoclonal Antibodies and Methods for Epidemiological Studies). 1990. Goteborg, Sweden. Doctoral Dissertation) and the determination of the presence of diarrhea signs was evaluated according to the severity with the following scale: 0 no diarrhea; 1 loss of the consistency of the feces but without wet tail; 2 region perianal and tail wetted and; 3 tail, paws and low abdomen wetted and with inactive appearance (Arredondo L J, Zaragoza S, Domínguez M, Willms K, López-Vidal Y, Cravioto A. Desarrollo de un nuevo Modelo Animal Experimental Hámster Sirio Dorado para el estudio de la infección por *Escherichia coli* enterotoxigénica (ETEC). Enf Infec Microbiol. 1997; 17(2):43-46).

We also characterized the immune response obtained for both studied groups for which cells from the spleen, lymphatic cervical ganglions, inguinal lymphatic ganglions and Peyer patches were obtained from mice on day 7 after the challenge with ETEC H10407. The adjusted cell suspensions obtained from each organ, were grown in the presence of antigens of CLE.

At the end of the cellular proliferation, the cells were labeled using antibodies to identify surface markers such as CD3, CD4 and CD8 and for the identification of intracellular cytokines such as IFN-gamma, IL-4 and IL-10. Once the cells were labeled, they were analyzed by flow cytometry.

The results showed that in relation to the excretion of ETEC, it was observed that on day 1, in both groups of animals positive coprocultures occurred at 100%, In the third day the positive coprocultures were of 75% for the control group and 50% in the group immunized with the peptide CLE. The presence of diarrhea in mice after the infection with ETEC was observed only with a change of consistency of the feces for the CLE-immunized and control groups, which continued to the fourth day in the latter group but from the fifth day, the consistency in feces was normal in all mice. These results can be appreciated in more detail in FIG. 1, which presents as a summary the follow up of mice after infection with ETEC H10407.

As for the evaluation of the immune response it was found that the response of T CD4+ and T CD8+ lymphocytes was slightly higher for the group immunized with CLE compared to the control group and it is necessary to emphasize that the increase of T CD4+ lymphocytes was about 2-fold in Peyer patches with regard to control group as it can be seen in FIG. 2.

Figure 3:
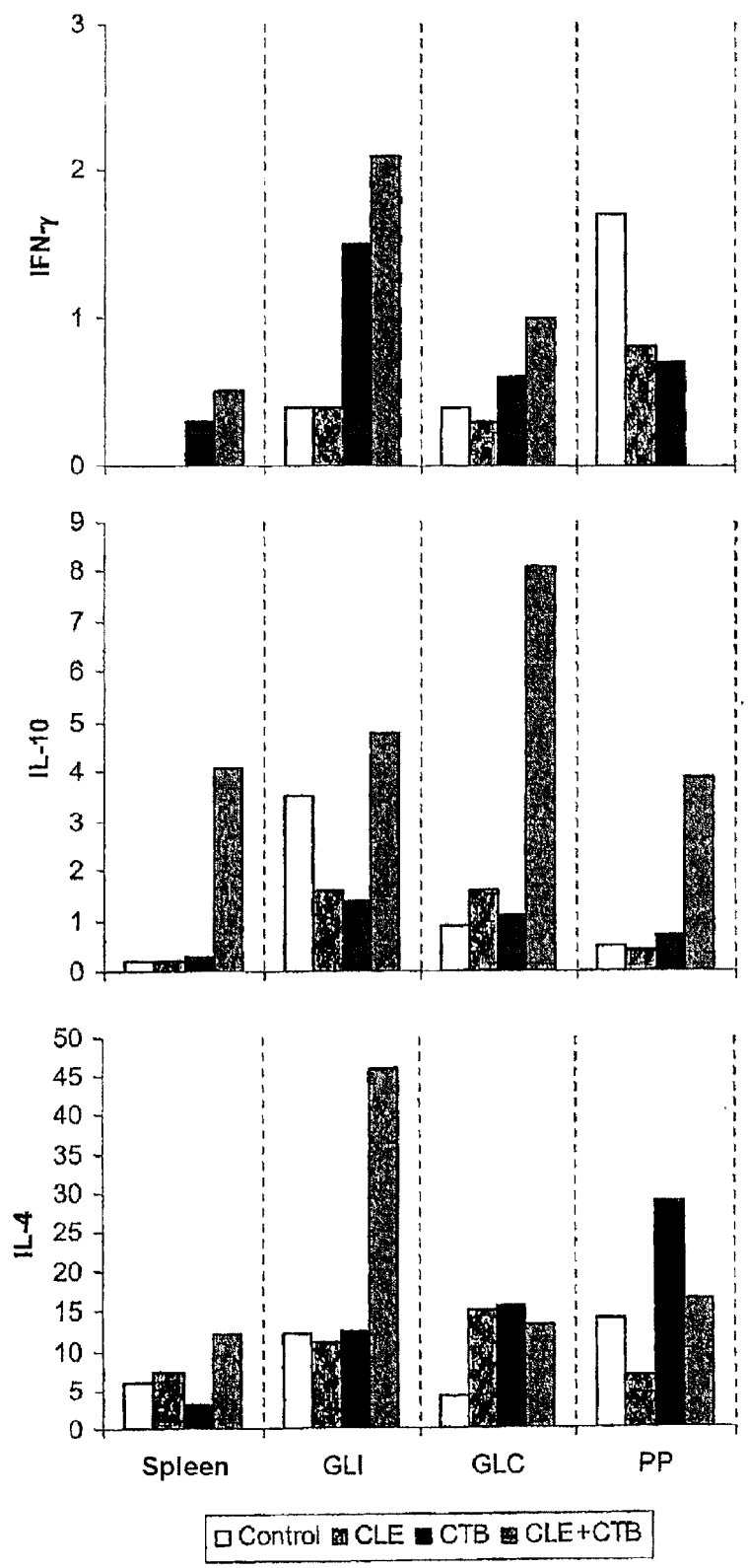
FIG. 3 shows a integral graph where the percentage of cells producing intracellular cytokines of lymphocytes specific to vaccine obtained from spleen, inguinal lymphatic ganglions, lymphatic cervical ganglions and Peyer patches belonging to mice immunized with CLE, CTB or the vaccine was analyze. From the graph it can be observed that cytokines IL-4 and IL-10 were mainly produced for animals vaccinated in all the organs of study, but a low production of INF-gamma was also observed.

As for cytokines response, a predominant production of IL-4 and IL-10 was observed in the group immunized with CLE, an increase being observed in the production of IL-4 of about 2.6 times in lymphatic cervical ganglions in the group immunized with CLE relative to the control and of 0.8 times in the production of IL-10 in the same organ, which is illustrated in FIG. 3.

Example 2

Demonstration of the Ability to Elicit an Immune Response Against ETEC with Adjuvant CTB Mice were immunized with CTB at a rate of 6 µg/mL by administering intranasally a volume of 7.5 µL and the control group was orally administered with a phosphate buffered solution, following the same methodology described in Example 1.

The obtained results are as follows: relative to the excretion of ETEC, it was observed that on day 1, both the control group and the group immunized with CTB exhibited positive coprocultures in 100%. To the third day the positive coprocultures were 75% for the control group and of 50% for the group immunized with CTB with a response similar to the obtained in mice immunized with CLE of the Example 1 being observed. Similarly to that observed for the mice immunized with CLE, those immunized with CTB exhibited inconsistency of feces up to the third day, but after the fourth day the consistency in the feces was normal in the CTB group and the control group as it can be observed in more detail in FIG. 1.

With this it was demonstrated that CTB has the ability to provide certain protection against infection caused by ETEC, but this protection it is not sufficient to counteract the signs of illness in mice such as the inconsistency of feces. As for the immune response it was observed that the subpopulation of T CD4+ increased 0.4 times in spleen in the group immunized with CTB relative to the control but T CD8+ subpopulation was very similar to the control group in the studied organs as can be observed in FIG. 2. The cytokines profile showed a preferential increase of IL-4 with a difference of 2.7 times being observed in lymphatic cervical ganglions and of 1.1 times in Peyer patches with regard to the control group. However, a considerable response of INF-gamma was obtained in inguinal lymphatic ganglions as it can be observed in FIG. 3. This demonstrates that the CTB, when it is administered alone to mice by intranasal route, induces an increase of immune response cells and cytokines of the predominant type Th1 such as IFN-gamma, thereby stimulating an immune cellular response, and it has already described that the protective response against ETEC infection is of humoral type.

Example 3

Vaccine developed in the present disclosure containing the peptide CLE identified in SEQ ID NO: 1 was used in a 8:1 ratio of CLE:CTB administered intranasally in a pharmacologically effective dose, that in this case was adjusted to the weight of the experimental animals, with a final concentration of 50 µg/mL added with CTB at doses of 6 µg/mL, administering a volume of 7.5 µL following the same methodology of Examples 1 and 2.

The obtained results were the following: relative to the excretion of ETEC, it was observed that on day 1, both the control group and the group immunized with the vaccine exhibited positive coprocultures in 100%. At third day the positive coprocultures were 75% for the control group and of 25% for the group immunized with the vaccine. The presence of diarrhea in the mice after the infection with ETEC was observed only with a change of consistency of the feces for the control groups, and this event did not appear in the group immunized with the vaccine as can be observed in FIG. 1.

It was possible to determine that the vaccine developed in the present disclosure exhibits a synergistic effect between the peptide CLE and the adjuvant CTB for the protection conferred against diarrhea caused by ETEC. With regard to the control group, the group immunized with the vaccine presented an increase of T CD4+ lymphocytes of 0.5 times in the spleen and of 5.7 times in Peyer patches. This increase was observed also for the T CD8+ lymphocytes in the group immunized with the vaccine with 0.1 times higher in the spleen and 1.8 times higher in Peyer patches; when comparing to the control group as is observed in FIG. 2.

IL-4 production showed a considerable increase for the group immunized with the vaccine mainly in spleen and in inguinal lymphatic ganglions of 1 and 2.8 times higher, respectively, compared to the control group. The response in lymphatic cervical ganglions and in Peyer patches for the group immunized with the vaccine showed an increase of IL-4 production in comparison to the control group of 2.1 and 0.2 times higher respectively.

As for the response to IL-10, an increase of this cytokine was observed in all groups with regard to the control, although this increase was lower than that observed for IL-4. The group that showed a higher increase was that of Example 3 immunized with the vaccine compared to the control group which is of 19.5, 0.4, 8 and 6.8 times more in spleen, lymphatic cervical ganglions, inguinal lymphatic ganglions and Peyer patches, respectively. The highest percentage of IL-10-producing cells was obtained in lymphatic cervical ganglions being 8.1% higher in the group immunized with the vaccine.

Finally, although the percentages of producing cells of IFN-gamma were very poor in all the studied organs, an increase was observed in cervical and inguinal lymphatic ganglions with regard to the control group of 1.5 and 4.3 times respectively. Both in the spleen and in Peyer patches differences were not observed in the response of IFN-gamma as can be observed in FIG. 3.

These results indicate that the intranasal administration of the vaccine containing the peptide CLE added with CTB in a ratio of 8:1 respectively in a pharmaceutically acceptable vehicle has the ability to elicit a protective response of T lymphocytes T principally CD4+ in sites of immune response as the Peyer patches, which is of great utility because these are located in the small intestine which is the target site of ETEC infection. Also, the vaccine generated the production of cytokines such as IL-4 and IL-10 distinctive of a response of type Th2 that stimulates an immune response of humoral type that is the principal protective defense against illness caused by ETEC.

From the obtained results from Examples 1, 2 and 3 it can be concluded that the protection conferred by CLE when it is administered in mice by intranasal route increases when it is administered in a formulation that contains an adjuvant, which in this case is the adjuvant CTB so that there is an synergistic effect between these two components of the vaccine.

Example 4

Female, 6 to 8 weeks old, Syrian golden Hamsters were intranasally immunized with peptide CLE corresponding to SEQ ID NO: 1 at a dose of 50 μg/mL added with CTB at a dose of 6 μg/mL by administering a volume of 7.5 μL of each component. Each hamster was immunized on day 0, 7 and 28. Blood samples by retrorbital route and samples of saliva were collected placing small strips of cellulose in the oral cavity, before the first immunization and 7 days after the last immunization. To the hamster control group was administered with a phosphate buffered solution.

To evaluate the conferred protection, parameters such as the excretion of ETEC in feces by means of coproculture and identification by means of hemagglutination test in the presence of D-mannose were determined as was already reported (López-Vidal Y. Colonization Factor antigens of Enterotoxigenic *Escherichia coli* (Monoclonal Antibodies and Methods for Epidemiological Studies). 1990. Goteborg, Sweden. Doctoral Dissertation) and the determination of the presence of signs of diarrhea which was evaluated in accordance to severity: 0, without diarrhea; 1, loss of the consistency of the feces but without wet tail; 2, region perianal and tail wetted and; 3, tail, paws and low abdomen wetted and with inactive appearance (Arredondo L J, Zaragoza S, Domínguez M, Willms K, López-Vidal Y, Cravioto A. Desarrollo de un nuevo Modelo Animal Experimental Hámster Sirio Dorado para el estudio de la infección por *Escherichia coli* enterotoxigénica (ETEC). Enf Infec Microbiol. 1997; 17(2):43-46).

To evaluate the immune protective response, the antibody titres were determined by ELISA against: CLE, fimbria CFA/I and against CTB and LT. And to determine the ability of these antibodies to agglutinate ETEC having different types of fimbria belonging to the CFA/I family an essay of agglutinative capacity was carried out with a suspension of formalin inactivated bacteria ($1 \times 10^8$ CFU) expressing fimbria CFA/I and sera from hamsters immunized with the vaccine and infected with ETEC expressing CFA/I. Furthermore, the neutralizing activity of serum anti-CTB antibodies from hamsters immunized and challenged against cholera toxin (CT) and against LT (5 μg/ml) by cellular permeability in New Zealand rabbits, was determined.

The obtained results demonstrated regarding the excretion of ETEC and the presence of signs of diarrhea that the average of duration of diarrhea caused by ETEC was 3 times higher in the control hamsters than in the immunized hamsters. The average percentage of ETEC excretion increased 2.5 times in the control group as it shows in FIG. 4.

Regarding the antibody titre against CLE, CFA/I and enterotoxins by means of ELISA, the levels of IgG antibodies, in hamsters immunized with the vaccine and control hamsters were compared, after being infected by ETEC expressing CFA/I; the differences showed to be significant against CLE, but not against CFA/I which is shown in FIG. 5. On the other hand, high titres were detected against CLE, CFA/I, CTB from *V. cholerae* and LT from ETEC. These titres remained constant, before and after the oral infection, with ETEC expressing CFA/I as is shown in FIG. 6. Also, it was found that these anti-CLE antibodies were capable of agglutinating significantly to the whole bacterium, which expresses CFA/I at titre of 2.6 and the antibodies against CTB, at titre of 2; they were capable of neutralizing in 100% the activity of (5 μg/ml) the toxins LT and CT.

These results demonstrate the effectiveness of the use of the intranasal vaccine against diarrhea caused by ETEC since in the model of Syrian golden hamster high titres of antibodies were generated against CLE, CFA/I, LT from ETEC and CTB from *V. cholerae*, in addition that these antibodies were capable of inducing protection from the diarrhea caused by ETEC expressing CFA/I.

Finally, being ETEC an important causal agent of infantile diarrhea and of the traveler on a global scale, its identification is not performed routinely in the laboratory, partly due to the need to provide a rapid and opportune treatment, nevertheless, the peptide of the SEQ ID NO: 1 disclosed herein, is found as an immunodominant epitope in strains of ETEC belonging to the CFA/I family, for this reason it would be an excellent candidate for the development and making of a diagnosis reagent specific for this family of ETEC.

What is claimed is:

1. The isolated peptide common linear epitope (CLE) consisting of the amino acid sequence set forth in SEQ ID NO: 1 containing a terminal cysteine, wherein when administered by intranasal route to mammals, it generates an immune response in Peyer patches, inguinal, cervical lymphatic ganglions and in the spleen that confers protection from illness caused by enterotoxigenic *Escherichia Coli* (ETEC).

2. The isolated peptide CLE of claim 1, wherein the terminal cysteine confers to it the ability to form dimers, trimers and pentamers that increases its stability and favors its recognition for recipients of the immune system of mammals.

3. The isolated peptide CLE of claim 1, wherein the response of immunity consists of an increase of T CD4+ and T CD8+ lymphocytes.

4. The isolated peptide CLE of claim 3, wherein the increase of T CD4+ lymphocytes is about two times higher in Peyer patches.

5. The isolated peptide CLE of claim 1, wherein the response of immunity consists of an increase of the production of cytokines in cervical and inguinal lymphatic ganglions.

6. The isolated peptide CLE of claim 5, wherein the cytokines IL-4 and IL-10 provide a Th2 response developing a humoral protection against ETEC illness.

7. A vaccine composition against illness caused by ETEC consisting of the isolated peptide CLE consisting of the amino acid sequence set forth in SEQ ID NO: 1 associated with an adjuvant in a pharmaceutically acceptable vehicle for intranasal administration.

8. The vaccine composition of claim 7, wherein the association of the isolated peptide with the adjuvant is in ratio such that it allows to synergistically potentiate the immune protective response against ETEC illness.

9. The vaccine composition of claim 7, wherein the adjuvant is cholera toxin B subunit (CTB) in a ratio of 8 parts of isolated peptide to one part of adjuvant.

10. The vaccine composition of claim 7, wherein the intranasal administration provides protection in sites distal from the mucosa immune system.

11. The vaccine composition of claim 7, wherein the synergistic protective immune response consists in the ability to induce a T CD4+ lymphocytes response and to generate the production of cytokines such as IL-4 and IL-10 stimulating an immune response of humoral type against the illness caused by ETEC.

12. The vaccine composition of claim 10, wherein said sites distal from the immune system are Peyer patches, inguinal lymphatic ganglions and the spleen.

13. An intranasal vaccine against ETEC illness consisting of a composition of isolated peptide CLE consisting of the amino acid sequence set forth in SEQ ID NO: 1 with an adjuvant in a pharmaceutically acceptable vehicle.

* * * * *

SEQUENCE LISTING

<160> NUMBER OF SEQ ID NOS: 1

<210> SEQ ID NO 1
<211> LENGTH: 20
<212> TYPE: PRT
<213> ORGANISM: Escherichia coli
<220> FEATURE:
<221> NAME/KEY: DISULFID
<222> LOCATION: (20)..(20)

```
-continued

<400> SEQUENCE: 1

Tyr Ser Pro Ala Ser Lys Thr Phe Glu Ser Tyr Arg Val Met Thr Gln
1               5                   10                  15

Val His Thr Cys
            20
```